United States Patent
Kim et al.

(10) Patent No.: US 7,184,815 B2
(45) Date of Patent: Feb. 27, 2007

(54) SYSTEM AND METHOD FOR SELECTION OF MORPHOLOGY TEMPLATES

(75) Inventors: Jaeho Kim, Redmond, WA (US); Joseph Bocek, Seattle, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 109 days.

(21) Appl. No.: 10/787,540

(22) Filed: Feb. 26, 2004

(65) Prior Publication Data

US 2005/0192506 A1   Sep. 1, 2005

(51) Int. Cl.
*A61B 5/0402* (2006.01)

(52) U.S. Cl. .................. 600/509; 600/515; 600/516; 600/517; 600/518

(58) Field of Classification Search ........ 600/508–509, 600/515–518; 607/28; 128/923
See application file for complete search history.

(56) References Cited

U.S. PATENT DOCUMENTS

| | | | |
|---|---|---|---|
| 5,000,189 A | 3/1991 | Throne et al. | |
| 5,217,021 A | 6/1993 | Steinhaus et al. | |
| 5,331,966 A | 7/1994 | Bennett et al. | |
| 5,447,519 A | 9/1995 | Peterson | |
| 5,779,645 A | 7/1998 | Olson et al. | |
| 5,817,027 A | 10/1998 | Arand et al. | |
| 5,857,977 A | 1/1999 | Caswell et al. | |
| 5,871,512 A | 2/1999 | Hemming et al. | |
| 5,891,176 A | 4/1999 | Bornzin | |
| 6,052,620 A | 4/2000 | Gillberg et al. | |
| 6,076,014 A | 6/2000 | Alt | |
| 6,449,503 B1 | 9/2002 | Hsu | |
| 6,522,923 B1 | 2/2003 | Turcott | |
| 6,567,701 B2 | 5/2003 | Vonk | |
| 6,615,083 B2 | 9/2003 | Kupper | |
| 2002/0183637 A1* | 12/2002 | Kim et al. .......... | 600/510 |
| 2002/0183837 A1 | 12/2002 | Kim et al. | |
| 2003/0181818 A1 | 9/2003 | Kim et al. | |
| 2003/0195572 A1 | 10/2003 | Bocek et al. | |
| 2004/0243014 A1* | 12/2004 | Lee et al. ......... | 600/510 |
| 2005/0137485 A1* | 6/2005 | Cao et al. .......... | 600/510 |

OTHER PUBLICATIONS

St. Jude Medical. Excerpt from: *Model 3510 Programmer with Model 3307 Software Reference Manual.* Section (3): *Programming Tachy Detection and Therapy Parameters*, pp. 3-26-3-31. 2001 St. Jude Medical Cardiac Rhythm Management Division. (4 total sheets, best copy available).

* cited by examiner

*Primary Examiner*—Robert E. Pezzuto
*Assistant Examiner*—Jessica L. Reidel
(74) *Attorney, Agent, or Firm*—Hollingsworth & Funk, LLC

(57) ABSTRACT

A template selection method involves providing a plurality of templates representing a type of cardiac event. One or more characteristics of each template are evaluated. The evaluations are compared and a template is selected as a current template based on the comparison.

33 Claims, 16 Drawing Sheets

Slope is flat

SYSTEM AND METHOD FOR SELECTION OF MORPHOLOGY TEMPLATES

FIELD OF THE INVENTION

The present invention relates generally to implantable medical devices and, more particularly, to selection of templates characterizing various types of cardiac events.

BACKGROUND OF THE INVENTION

Rhythmic contractions of a healthy heart are normally controlled by the sinoatrial (SA) node, specialized cells located in the upper right atrium. The SA node is the normal pacemaker of the heart, and when functioning normally, the heart produces rhythmic contractions and is capable of pumping blood throughout the body. However, due to disease or injury, the heart rhythm may become irregular resulting in diminished blood circulation. Arrhythmia is a general term used to describe heart rhythm irregularities arising from a variety of physical conditions and disease processes. Cardiac rhythm management systems, such as implantable pacemakers and implantable cardioverter/defibrillators (ICDs), have been used as an effective treatment for patients with serious arrhythmias. These systems typically comprise circuitry to sense electrical signals from the heart and a pulse generator for delivering electrical stimulation pulses to the heart. Leads extending into the patient's heart are connected to electrodes electrically coupled to the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce contractions of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contractile response in heart tissue, the contractile response is typically referred to as capture, and the electrical cardiac signal corresponding to capture is denoted the evoked response. Superimposed on the evoked response may be a pacing artifact signal that includes a signal associated with post pace residual polarization. The magnitude of the pacing artifact signal may be affected by a variety of factors including lead polarization, after potential from the pace pulse, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. If the pace pulse energy is too low, the pace pulses may not reliably produce a contractile response in the heart resulting in ineffective pacing. If the pace pulse energy is too high, the result may be patient discomfort as well as shorter battery life. Thus, accurate determination of the capture threshold is required for efficient pace energy management.

Capture verification has been accomplished by examining the cardiac waveform following a pacing pulse. Such an examination may involve, for example, comparison of the cardiac waveform following the pace pulse to a morphology template characterizing a captured response. If the cardiac waveform matches the captured response template, then capture may be declared.

Morphology templates may also be used to detect and/or classify types of cardiac tachyarrhythmias. Implantable cardioverter/defibrillators (ICDs) have been used to deliver effective treatment for patients with serious tachyarrhythmias. ICDs are able to treat such arrhythmias with a variety of tiered therapies. These tiered therapies include providing anti-tachycardia pacing or cardioversion energy for treating ventricular tachycardia, and/or delivering defibrillation energy to the heart for treating ventricular fibrillation. To effectively deliver an appropriate therapy, the ICD may first identify the type of arrhythmia that is occurring. To identify the type of arrhythmia, the ICD may compare sensed cardiac signals to a previously stored morphology template.

Detecting and classifying various types of cardiac events using morphology templates depends in part upon how accurately the morphology template represents the type of cardiac event. For the reasons stated above, and for other reasons stated below which will become apparent to those skilled in the art upon reading the present specification, there is a need in the art for methods and systems that reliably and accurately characterize cardiac waveforms representing various cardiac events. There exists a further need for such an approach that is adaptive and accommodates to changes in cardiac signal morphology over time. The present invention fulfills these and other needs.

SUMMARY OF THE INVENTION

The present invention involves a method and system for selecting a template representative of a particular type of cardiac event. In accordance with one embodiment of the invention, a template selection method involves providing a plurality of templates representing a type of cardiac event. One or more characteristics of each template are evaluated. The evaluations are compared and a template is selected as the current template based on the comparison.

Another embodiment of the invention involves a method for selecting a cardiac rhythm template. The method includes providing a plurality of templates representing a type of cardiac rhythm. One or more cardiac beats associated with the type of cardiac rhythm are detected. The accuracy of each template is determined using the one or more cardiac beats. The accuracies of the plurality of templates are compared and a template is selected as a current template based on the comparison.

In yet another embodiment of the invention, a medical device includes a sensing system configured to sense cardiac signals associated with cardiac events. The medical device further includes a processor coupled to the sensing system and configured to provide a plurality of templates representing a type of cardiac event, evaluate one or more characteristics of each template, compare the evaluations, and select a template as a current template representing the type of cardiac event based on the comparison.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 14A–4F are flowcharts illustrating methods of template evaluation in accordance with embodiments of the invention.

Figure 1:
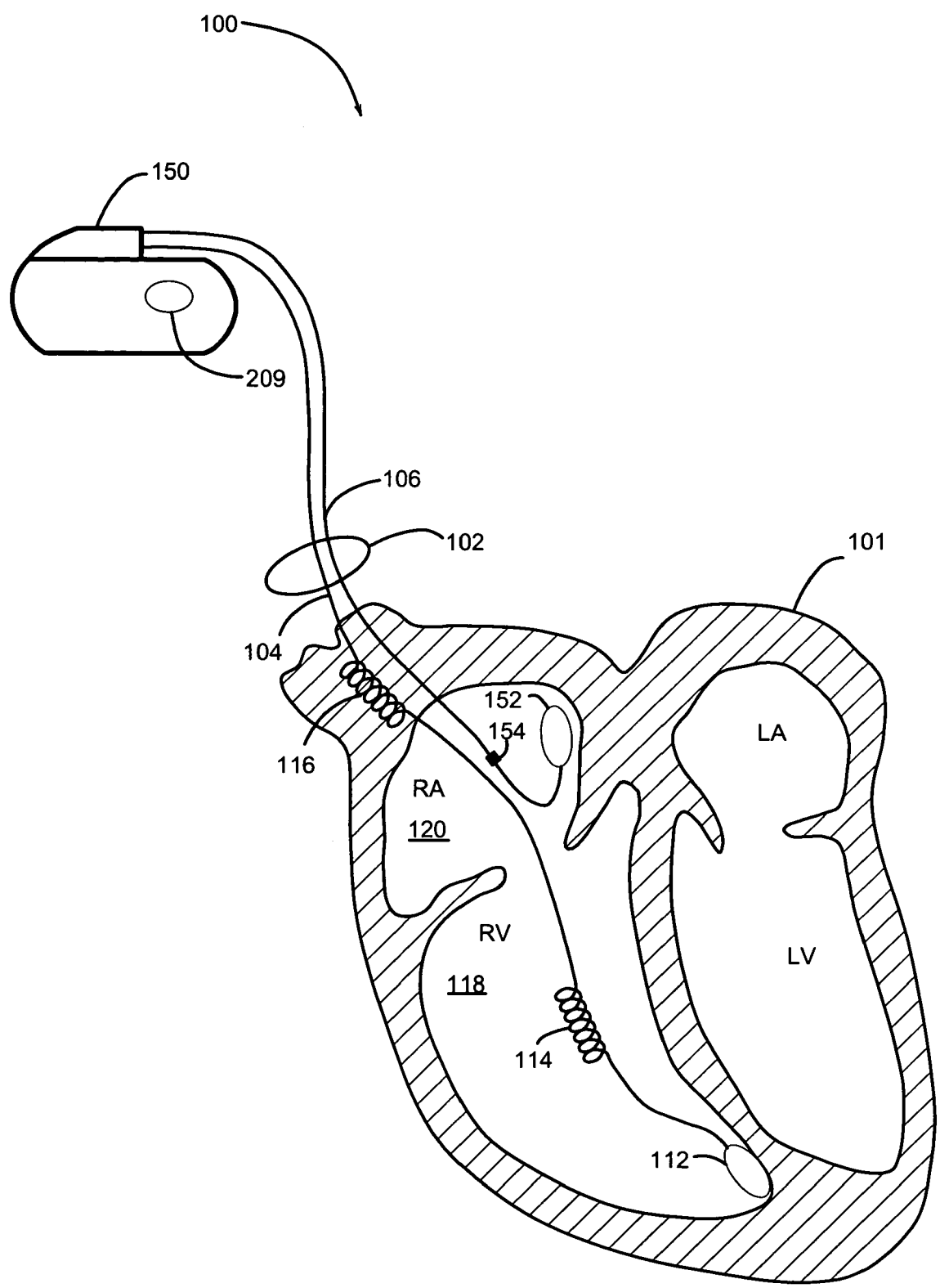
FIG. 1 is a partial view of an implantable medical device with an endocardial lead system extending into atrial and ventricular chambers of a heart in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings that form a part hereof, and in which are shown, by way of illustration, various embodiments by which the invention may be practiced. It is to be understood that other embodiments may be utilized, and structural and functional changes may be made without departing from the scope of the present invention.

A variety of cardiac rhythm management devices may be used to detect and treat various arrhythmias of the heart. Such devices include, for example, pacemakers for treating heart rhythms that are too slow (bradycardia), and cardioverter/defibrillators for detecting and treating fast cardiac arrhythmias, such as ventricular tachycardia (VT) and/or ventricular fibrillation (VF). Pacemakers regulate the heart's rhythm by delivering low energy electrical stimulation to the heart to produce contraction of the heart tissue. Cardioverter/defibrillators treat cardiac tachyarrhythmia or fibrillation by delivering high energy electrical stimulation to the heart to terminate or mitigate arrhythmias.

Cardiac rhythm management (CRM) systems may be used to detect various types of cardiac events through examination of the electrical signals produced by the heart. In accordance with one methodology, cardiac events signals can be detected by comparing sensed cardiac signals to signal patterns characterizing a particular type of cardiac event. The signal patterns characterizing various types of cardiac events may be represented by signal morphology templates stored in the cardiac rhythm management system.

A morphology template representing a particular type of cardiac event may initially be generated by sensing one or more cardiac signals representative of the particular type of cardiac event and forming a characterization of the representative cardiac signal or signals. The characterization of the representative signal is denoted herein as a template, and the signals used to generate the template are described as template beats or template signals. A template may be formed, for example, by extracting samples, feature points and/or morphology characteristics from the template signals and storing the samples, feature points and/or morphology characteristics as the morphology template representative of the particular type of cardiac event. Morphology templates may be used to evaluate subsequent cardiac signals to detect and classify various types of cardiac events.

For example, cardiac rhythm management systems may use morphology templates to detect and classify various types of cardiac arrhythmias. Cardiac arrhythmia can be broadly categorized as an abnormality of the heart rhythm. Arrhythmia can originate in the heart's atria producing supraventricular tachyarrhythmias (SVTs), including atrial fibrillation (AF) and atrial flutter (AFL). Arrhythmia may originate in the heart's ventricles, producing ventricular tachycardias (VT) or ventricular fibrillation (VF).

Morphology templates may be used to determine if a fast cardiac rhythm of ventricular beats originates in the ventricles or is supraventricular in origin. In one implementation, a detected fast cardiac rhythm may be compared with a stored template characterizing a ventricular beat of supraventricular origin, referred to herein as a patient's supraventricular rhythm (SVR). If the fast cardiac rhythm matches the SVR template, the rhythm is classified as supraventricular in origin. If the fast cardiac rhythm does not match the SVR template, the cardiac rhythm may be classified as a ventricular tachyarrhythmia. Discriminating arrhythmias that are supraventricular in origin from arrhythmias originating in the ventricles allows the cardiac rhythm management system to deliver an appropriate therapy to treat the arrhythmia.

Templates characterizing a patient's supraventricular rhythm (SVR) may be generated using intrinsic, non-paced beats to form the template. Various methods for generating an SVR template for use in a cardiac rhythm management system are described in commonly owned U.S. patent applications Ser. No. 09/845,987, filed Apr. 30, 2001, Ser. No. 10/105,875, filed Mar. 25, 2002, and commonly owned U.S. Pat. No. 6,449,503 all of which are incorporated herein by reference.

Curvature-based methods for forming templates characterizing various types of cardiac events are described in commonly owned U.S. Pat. No. 6,684,100 which is incorporated herein by reference. Methods and systems for generating templates based on the location of one or more waveform features is described in commonly owned U.S. patent application Ser. No. 10/448,260, filed May 28, 2003, which is incorporated herein by reference.

When the heart is being intermittently or constantly paced, a sufficient number of consecutive intrinsic beats may not be readily available for template generation. Generally, paced beats may not be used to characterize SVR. When intrinsic beats are unavailable or are rarely produced, additional processes may be required to obtain an SVR template. Methods of characterizing SVR for patients requiring intermittent or constant pacing are described in commonly owned U.S. patent applications Ser. No. 10/121,944, filed Apr. 12, 2002, and Ser. No. 10/278,746, filed Oct. 23, 2002 both of which are incorporated herein by reference.

Generation of an SVR morphology template may involve extraction of a plurality of samples, feature points and/or morphology characteristics from one or more cardiac signals representative of the patient's supraventricular rhythm. A subsequently detected cardiac rhythm may be classified as a supraventricular rhythm if the samples, feature points and/or morphology characteristics of the subsequently detected cardiac signal are similar to the corresponding samples, feature points and/or morphology characteristics of the SVR morphology template.

Another approach to template generation involves identifying the relative position of representative cardiac signal features. Morphology templates based on this approach may be created by defining and identifying target regions associated with cardiac waveform features. One or more target regions may be used to establish a template representing a particular type of waveform morphology, such as a normally conducted cardiac rhythm, an arrhythmogenic beat, or captured beat, for example. A cardiac waveform may be classified as matching the template if a selected number of the cardiac waveform features fall within the target regions of the template.

When the heart is paced, a function that may be implemented in the cardiac rhythm management system involves recognition of a cardiac signal indicative of a contraction of heart tissue following delivery of a pacing stimulation. When a pace pulse produces a contraction, the contractile response is typically referred to as capture. The electrical signal produced by the contraction is denoted the evoked response. Capture may be detected, for example, by sensing the electrical activity of the heart following a pacing stimulation and detecting an evoked response.

Detection of the evoked response may be complicated by a large pacing artifact signal superimposed on the much smaller evoked response signal. The combination of the evoked response signal and the superimposed pacing artifact signal is referred to herein as the captured response. Detection of the evoked response signal may involve, for example, canceling the pacing artifact signal from a captured response.

One capture detection method involves the use of capture-related templates. For example, a pacing artifact template may be cancelled from a cardiac response detected within a capture detection timing window established subsequent to the delivery of a pacing stimulation. The resulting pacing artifact cancelled waveform may be evaluated to detect an evoked response. One approach involves comparing the pacing artifact cancelled waveform to an evoked response template. If the pacing artifact cancelled waveform matches the evoked response template, capture is declared.

Pacing artifact templates may be generated, for example, by delivering a pacing stimulation at a sufficiently low energy or during a myocardial refractory period to ensure that capture does not occur. This procedure allows a pacing artifact to be generated without an accompanying evoked response. The samples of the resulting pacing artifact signal, or selected features thereof, may be extracted and stored as the pacing artifact template.

Captured response templates may be formed, for example, by delivering pace pulses to the heart at an energy that exceeds the capture threshold, thereby ensuring a contraction of the heart tissue. The cardiac signal associated with the contraction may be detected and used to generate a captured response template.

A method for forming an evoked response template involves canceling the pacing artifact template from the captured response template. Capture-related templates, including those described above, can be used to detect subsequent capture events. Methods and systems for generating capture-related templates and/or detecting capture using capture-related templates are described in commonly owned U.S. patent applications Ser. No. 10/335,599, filed Dec. 31, 2002, Ser. No. 10/335,534, filed Dec. 31, 2002, Ser. No. 10/278,732, filed Oct. 23, 2002, Ser. No. 10/733,869, filed Dec. 11, 2003, all of which are hereby incorporated herein by reference.

Embodiments of the invention involve methods and systems for selecting templates to characterize various cardiac events. Sensed cardiac signals may be evaluated and/or classified by comparing the signals to the templates. A device capable of implementing the template selection approaches described herein is depicted in FIG. 1. FIG. 1 shows one embodiment of a cardiac rhythm management system (CRM) 100 that includes an implantable cardiac pulse generator 150 electrically and physically coupled to can 209 electrode and to an intracardiac lead system 102. The intracardiac lead system 102 is implanted in a human body with portions of the intracardiac lead system 102 inserted into a heart 101. The intracardiac lead system 102 is used to detect electrical signals produced by the heart 101 and to provide electrical energy to the heart 101 under certain predetermined conditions to treat cardiac arrhythmias.

The intracardiac lead system 102 illustrated in FIG. 1 includes a number of intracardiac pace/sense electrodes and defibrillation electrodes. The intracardiac lead system 102 includes a ventricular lead system 104 and an atrial lead system 106. In the particular embodiment illustrated in FIG. 1, the ventricular lead system 104 shown is implemented as an integrated pace/shock lead. The ventricular lead system 104 includes an SVC-coil 116, an RV-coil 114, and an RV-tip electrode 112. The RV-coil 114 is spaced apart from the RV-tip electrode 112, which is a pacing electrode. In another exemplary configuration, one or more additional electrodes, e.g., an RV-ring electrode, may be included in the ventricular lead system 104. In this configuration, the RV-ring electrode and the RV-tip electrode 112 may be used for bipolar sensing of cardiac signals in the right ventricle and bipolar pacing of the right ventricle. The atrial lead system 106 depicted in FIG. 1 includes an A-tip electrode 152 and an A-ring electrode 154.

The intracardiac lead system 102 is positioned within the heart 101, with portions of the atrial lead system 106 extending into the right atrium 120 and portions of the ventricular lead system 104 extending into the right atrium 120 and right ventricle 118. In particular, the A-tip electrode 152 and A-ring electrode 154 are positioned at appropriate locations within the right atrium 120. The RV-tip electrode 112 and RV-coil 114 electrodes are positioned at appropriate locations within the right ventricle 118. The SVC-coil 116 is positioned at an appropriate location within the right atrium 120 or a major vein leading to the right atrium 120. The RV-coil 114 and SVC-coil 116 depicted in FIG. 1 are defibrillation electrodes.

The cardiac rhythm management system may employ a variety of lead configurations in addition to, or instead of, those depicted in FIG. 1. Intracardiac or extracardiac leads and associated electrodes may be positioned in, on, or about the heart in various configurations to electrically couple the heart to the pulse generator. In the exemplary embodiment illustrated in FIG. 1, electrodes are positioned in two heart chambers and may be used for dual chamber sensing and/or pacing of the heart. In other implementations additional pacing and/or defibrillation electrodes may be used and other lead configurations may be used. For example, a left heart lead system may be inserted through the coronary sinus to position one or more electrodes within the cardiac vasculature adjacent to the left ventricle and/or left atrium. The left heart lead system may also include an electrode positioned within the coronary sinus. Electrical access to the left ventricle and/or the left atrium may be used to provide three or four chamber pacing and sensing. Alternatively, fewer leads and/or fewer electrodes may be used, e.g., to implement single chamber pacing and sensing. Various additional intracardiac, extracardiac, and subcutaneous lead and electrode arrangements known in the art are also possible and are considered to be within the scope of the present system.

The embodiment illustrated in FIG. 1 is one example of a system that may be used for template selection according to embodiments of the present invention. It will be appreciated by those skilled in the art that other devices and systems may also be used to implement the template selection approaches described herein. Such devices may include, for example, a variety of implantable or patient-external therapeutic or diagnostic devices including pacemakers, cardiac monitors, cardioverter/defibrillators, single chamber pacemakers, multi-chamber pacemakers, multi-site pacemakers, rate adaptive pacemakers, biventricular pacing systems, and cardiac resynchronizers, among others.

Figure 2:
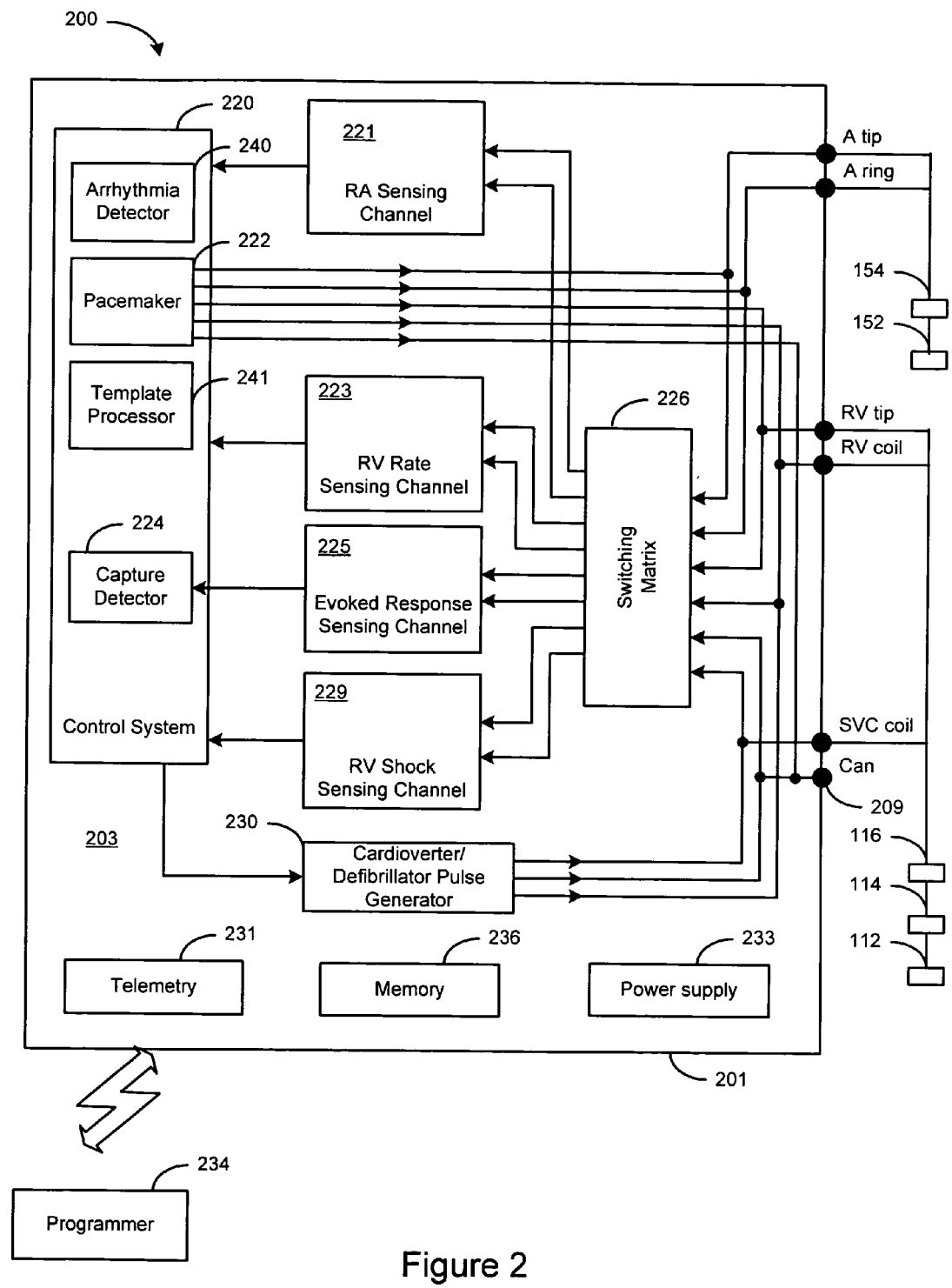
FIG. 2 is a block diagram of a cardiac rhythm management system in which template selection methods in accordance with embodiments of the invention may be implemented.

Referring now to FIG. 2, there is shown a block diagram of a cardiac rhythm management system 200 suitable for implementing the template selection methodology in accordance with embodiments of the invention. FIG. 2 shows a CRM system divided into functional blocks. It is understood by those skilled in the art that there exist many possible configurations in which these functional blocks can be arranged. The example depicted in FIG. 2 is one possible functional arrangement.

The CRM system 200 includes various components for sensing cardiac signals from a heart and delivering therapy, e.g., pacing pulses or defibrillation shocks, to the heart. The pulse generator (PG) 203 of the CRM system 200 may be encased and hermetically sealed in a housing 201 suitable for implanting in a human body. Power to the PG 203 is supplied by an electrochemical battery 233 that is enclosed within the housing 201. A connector block with lead terminals (not shown) is additionally attached to housing 201 to allow for the physical and electrical attachment of the intracardiac lead system conductors to the encased PG 203.

In one embodiment, the PG 203 is a programmable microprocessor-based system, including a control system 220 and a memory circuit 236. The memory circuit 236 stores parameters for various pacing, defibrillation, and sensing modes and may store data indicative of cardiac signals received by other components of the PG 203. The control system 220 and memory circuit 236 cooperate with other components of the PG 203 to perform operations involving template generation and selection according to the approaches of the present invention. The control system 220 may encompass various functional components, for example, a template processor 241, a pacemaker 222, an arrhythmia detector 240, and a capture detector 224, described in more detail below.

The memory circuit 236 may be used to store historical records of sensed cardiac signals and/or information about therapy delivered to the patient. The historical data may be used for various purposes, including diagnosis of patient conditions and/or to adjust the operations of the CRM system 200. Data stored in the memory 236 may be transmitted to an external programmer unit 234 as needed or desired.

Telemetry circuitry 231 may be coupled to the PG 203 to allow the CRM system 200 to communicate with an external programmer unit 234. In one embodiment, the telemetry circuitry 231 and the programmer unit 234 use a wire loop antenna and a radio frequency telemetric link to receive and transmit commands and data between the programmer unit 234 and the telemetry circuitry 231. In this manner, programming commands and/or data may be transferred between the control system 220 of the PG 203 and the programmer unit 234 during and after implant.

In the embodiment of the CRM system 200 depicted in FIG. 2, electrodes RA-tip 152, RA-ring 154, RV-tip 112, RV-coil 114, SVC coil 116, and can 209 are coupled through a switching matrix 226 to various sensing circuits. A right atrial sensing channel circuit 221 serves to detect and amplify electrical signals from the right atrium of the heart. Bipolar sensing in the right atrium may be implemented by sensing signals developed between the RA-tip 152 and RA-ring 154 electrodes. The switch matrix 226 is operated to couple the RA-tip 152 and RA-ring 154 electrodes to the RA sensing channel circuit 221 to effect bipolar sensing of right atrial signals. Alternatively, unipolar right atrial sensing may be accomplished by operating the switch matrix 226 to couple the RA-tip 152 and can 209 electrodes to the RA sensing channel circuit 221.

Cardiac signals sensed through the use of the RV-tip electrode 112 are right ventricular (RV) near-field signals and are referred to as RV rate channel signals herein. Bipolar rate sensing may be accomplished by operating the switch matrix 226 to couple the RV-tip 112 and the RV-coil electrodes 114 through the RV rate channel sensing circuitry 223. The rate channel signal may be detected, for example, as a voltage developed between the RV-tip 112 and the RV-coil 114 electrodes. The RV rate channel sensing circuitry 223 serves to sense and amplify the RV rate channel signal.

In an alternative configuration, unipolar RV sensing may implemented, for example, by coupling the RV-tip 112 and can 209 electrodes to the RV rate channel sensing circuitry 223. In this configuration, the rate channel signal is detected as a voltage developed between the RV-tip 112 to can 209 sensing electrodes.

The RV lead system may also include an RV-ring electrode (not shown in FIG. 2) used for bipolar pacing and sensing. If an RV-ring electrode is included in the lead system, bipolar sensing may be accomplished by sensing a voltage developed between the RV-tip 112 and RV-ring (not shown) electrodes.

Cardiac signals sensed through use of one or both of the defibrillation coils or electrodes 114, 116 are far-field signals, and are referred to as morphology or shock channel signals herein. In a preferred embodiment, the shock channel signal is detected as a voltage developed between the RV-coil 114 and the can electrode 209 or the can electrode 209 shorted to the SVC-coil 116. The switch matrix 226 is operated to couple the desired shock channel sensing vector, e.g., RV-coil to can, to the RV shock channel sensing circuitry 229. The RV shock channel circuitry 229 serves to sense and amplify the shock channel signal.

The outputs of the switching matrix 226 may also be operated to couple selected combinations of the electrodes to evoked response channel sensing circuitry 225 for capture detection. The evoked response (ER) channel sensing circuitry 225 serves to sense and amplify cardiac signals used to detect capture of the heart. The cardiac signals are coupled through the ER channel sensing circuitry 225 to a capture detector 224.

The capture detector 224 may detect capture by analyzing cardiac signals following a pacing pulse to determine if the pace pulse produced capture. In accordance with various embodiments of the invention, the capture detector 224 includes circuitry configured to detect an evoked response and verify capture using stored capture-related templates. If capture is not detected after a pace pulse is delivered, the capture detector 224 may communicate with the pacemaker 222 to initiate the delivery of a back-up pace pulse. The capture detector 224 may also be used in connection with a capture threshold test. In such a test, pace pulses may be delivered at decreasing energy levels until loss of capture is detected. The lowest pacing energy level that produces capture is identified as the capture threshold. The pacing stimulation energy may be adjusted based on the identified capture threshold.

The control system 220 receives signals from other components of the CRM system 200 and controls the operation of various CRM functions. The control system 220 includes a pacemaker 222 that controls delivery of low energy pacing pulses to one or more heart chambers. The pacemaker 222 communicates pacing signals to selected electrodes according to a preestablished pacing regimen under appropriate conditions.

Unipolar pacing of the right atrium may be accomplished, for example, by delivering pacing pulses between the RA-tip 152 and can 209 electrodes. Bipolar pacing of the right atrium may be accomplished by delivering pacing pulses between the RA-tip 152 and RA-ring 154 electrodes.

Right ventricular pacing may similarly be implemented using unipolar or bipolar configurations. Unipolar RV pacing involves, for example, pacing pulses delivered between the RV-tip 112 to can 209 electrodes. Bipolar pacing involves, for example, delivery of pacing pulses between the RV-tip 112 to RV-coil 114 electrodes. If an RV-ring electrode is present, bipolar pacing may be accomplished by delivering the pacing pulses to the RV-tip 112 and RV-ring (not shown) electrodes.

The CRM system 200 may include an arrhythmia detector 240 configured to detect a variety of arrhythmias. The arrhythmia detector 240 may detect and/or classify arrhythmia, based on morphological analysis of cardiac signals received from the RA and RV sensing channels 221, 223, 229. The arrhythmia detector may detect and/or classify arrhythmia by comparing sensed cardiac beats to stored templates characterizing arrhythmic beats and/or normal beats. In one example, discrimination between SVT and VT may be accomplished by comparing a sensed cardiac beat to a template characterizing the patient's normal supraventricular rhythm (SVR). In another example, the arrhythmia detector 240 may detect or classify an arrhythmia by comparing sensed cardiac beats to templates characterizing abnormal beats, such as ventricular tachycardia, atrial fibrillation and/or atrial flutter. Other arrhythmia detection methodologies, e.g., rate based or pattern based arrhythmia detection, are known in the art and may be implemented in the CRM 200. When an arrhythmia is detected by the arrhythmia detector 240, the control system 220 may communicate with the cardioverter/defibrillator pulse generator 230 to initiate therapy, including high energy shocks, to mitigate or terminate the arrhythmia.

The template selection processes in accordance with embodiments of the invention may be primarily implemented in the template processor 241. The template processor 241 communicates with the control system 220 and may generate templates, such as the arrhythmia-related and capture-related templates described herein. The generated templates may be stored in memory 236 of the pulse generator 203.

The stored templates may be updated periodically. A template update procedure may be initiated, for example, automatically or by an external template update command. A template update command may be made by a physician, and communicated to the pulse generator 203 through the external programmer 234, for example. An automatic template update procedure may involve periodically updating one or more templates without external initiation. For example, one or more templates may be updated daily, weekly, or according to another time basis. The template processor 241 may determine an optimal time for attempting a template update, e.g., during the patient's normal sleep time.

Embodiments of the invention are directed to methods for selecting a current template from a plurality of stored and/or newly generated templates. A template selection method in accordance with embodiments of the invention is, illustrated in the flowchart of FIG. 3. The method illustrated in FIG. 3 involves providing 310 a plurality of templates characterizing a particular type of cardiac event. The type of cardiac event may include a sensed cardiac beat, a paced cardiac beat, an arrhythmia-related event, a capture-related event, or any other type of cardiac event that may be characterized and/or analyzed using templates. The plurality of templates may be provided 310 by retrieving one or more stored templates from memory and/or generating one or more new templates.

Characteristics of the plurality of templates are evaluated 320. For example, the templates may be evaluated with respect to the accuracy of the templates at characterizing the particular cardiac event. Evaluating the accuracy of a template involves evaluating the degree to which the template is representative of a particular type of cardiac event. In other words, a more accurate template is one which can be used more successfully to detect a particular type of cardiac rhythm or cardiac event. The evaluations of the template characteristics, e.g., template accuracies, are compared 330 and a template is selected 340 as a current template based on the comparison.

Figure 3:
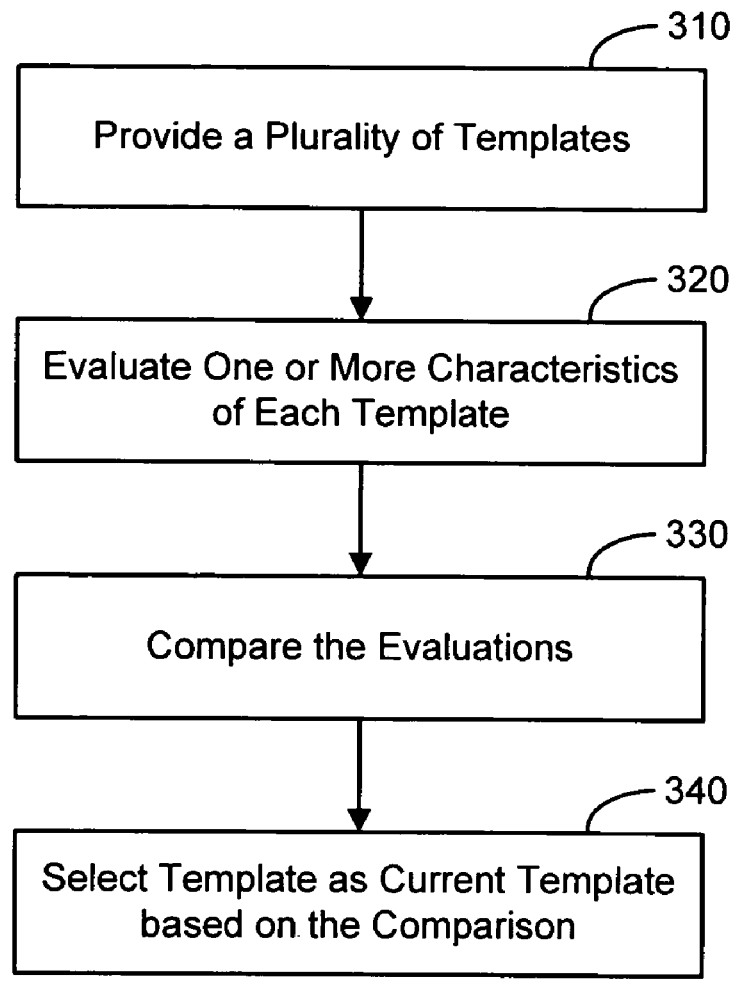
FIG. 3 is a flowchart of a template selection method in accordance with embodiments of the invention.

In one example, the method illustrated in FIG. 3 may be used to compare characteristics of a template previously stored as the current template to a newly generated template. One or more characteristics of the stored template and the newly generated template, e.g., accuracies of the templates, are evaluated. Accuracies of the templates may be evaluated, for example, by determining the similarities of the templates to one or more cardiac signals representative of the particular type of cardiac event represented by the templates. The evaluation of the stored template is compared to the evaluation of the newly generated template. A template is selected as the current template based on the comparison. A current template may be replaced if the evaluations of the template characteristics indicate the newly generated template is superior to the current template. Alternatively, a current template may be retained if the evaluations of the templates indicate that the current template is equal to or superior to the newly generated template.

Template evaluations may be performed using various processes. In one example, template accuracy may be determined by comparing the QRS widths (or other morphological characteristics) of the templates to QRS widths of one or more cardiac beats representative of a particular type of cardiac beat. In a preferred embodiment, described in greater detail below, samples or selected feature points of each template may be compared to corresponding samples or feature points of cardiac signals representative of a particular type of cardiac beat. In this implementation, a correlation coefficient or feature correlation coefficient may be calculated representing the overall correlation of the templates to the cardiac signals.

Figure 4:
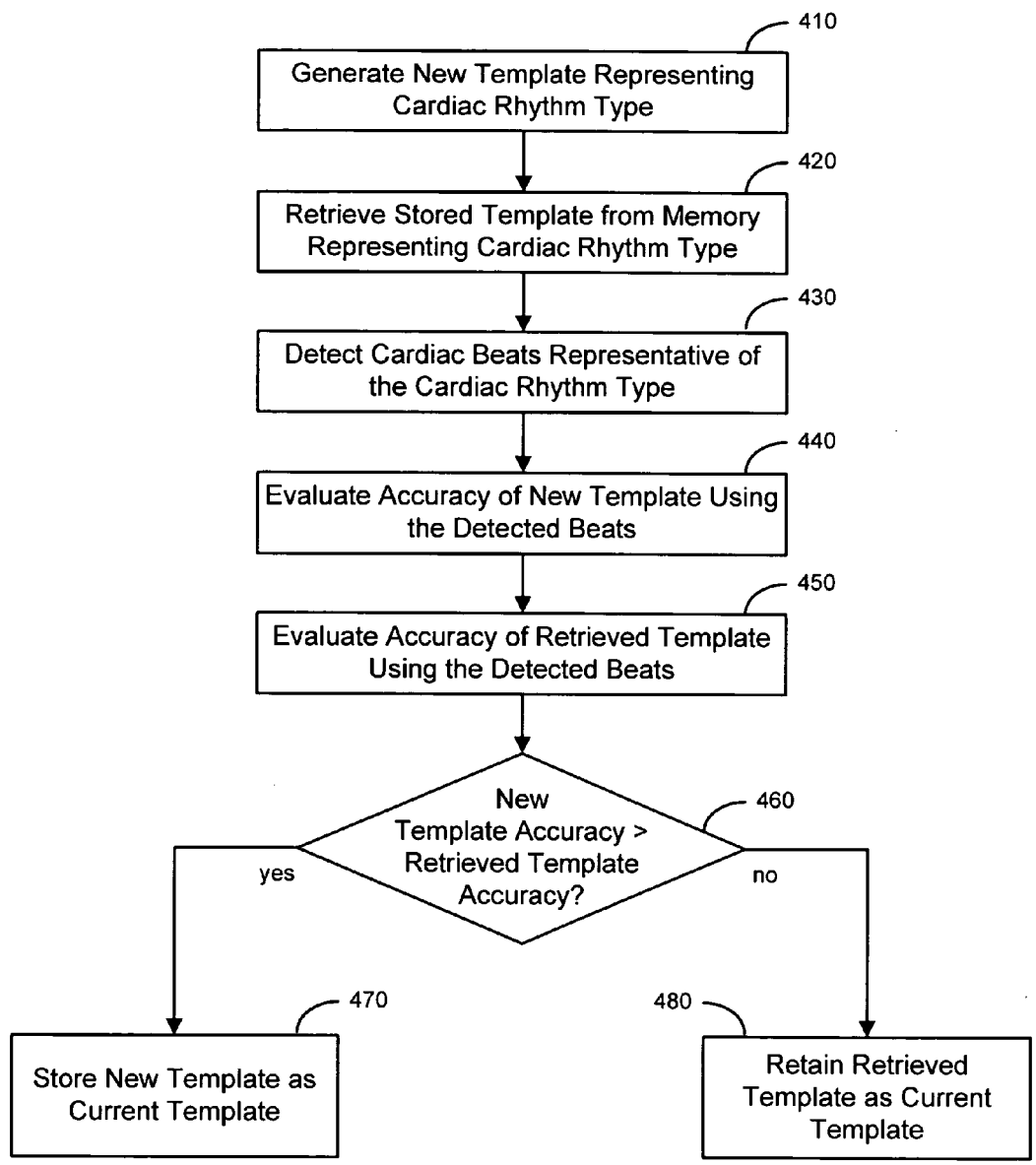
FIG. 4 is a flowchart of a method for selecting arrhythmia-related templates in accordance with embodiments of the invention.

Referring now to the flow chart of FIG. 4, a method of selecting arrhythmia-related templates in accordance with embodiments of the invention is illustrated. A plurality of templates characterizing a particular type of cardiac rhythm is generated 410. A stored template representing the cardiac rhythm type is retrieved 420 from memory. The generated and retrieved arrhythmia-related templates may characterize normal or arrhythmic cardiac beats. For example, the templates may characterize a patient's supraventricular rhythm (SVR). Such templates may be generated, for example, using the two channel approaches as described in commonly owned U.S. patent applications Ser. No. 09/845,987, Ser. No. 10/105,875, Ser. No. 10/121,944, Ser. No. 10/278,746, and U.S. Pat. No. 6,449,503 all previously incorporated herein by reference.

One or more cardiac beats representative of the type of cardiac rhythm are detected 430 and used to evaluate the templates. In order to determine if the cardiac beats are representative of the type of cardiac rhythm, the cardiac beats may be required to meet certain criteria, e.g., stability and/or rate criteria, etc. prior to using the beats for template evaluation.

The representative cardiac beats are used to evaluate 440 the accuracy of the newly generated template. The representative cardiac beats are then used to evaluate 450 the accuracy of the retrieved template. In one implementation, template accuracy is determined by evaluating the correlation between the representative cardiac beats and a template characterizing the type of cardiac rhythm. The accuracies of each of the templates are compared. If the accuracy of the newly generated template is greater than 460 the retrieved template, the newly generated template is stored 470 as the current template. When the accuracy of the retrieved template is greater than or equal to 460 the newly generated template, the retrieved template is retained 480 as the current template.

Figure 5:
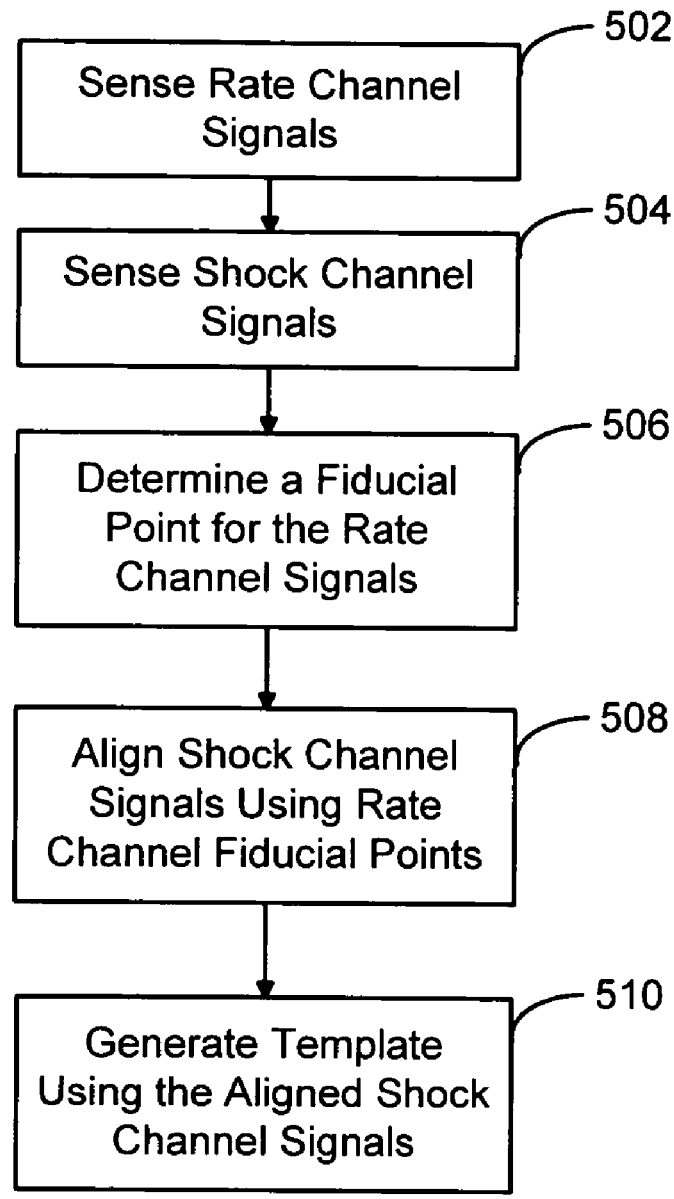
FIG. 5 is a flowchart of a method for generating morphology templates representative of a patient's supraventricular conducted rhythm (SVR) in accordance with embodiments of the invention.

FIG. 5 illustrates a two channel approach for generation of a morphology template representative of a patient's normal supraventricular conducted rhythm (SVR) according to embodiments of the invention. Such a template may be generated through multiple stages and may be regenerated or updated periodically as needed or desired.

An SVR template may be formed from a combination of one or more beats, wherein the combination represents the patient's intrinsic rhythm. Cardiac beats used to form the SVR template may be required to meet certain criteria, e.g., stability and rate criteria. If the cardiac beats meet the criteria, they are referred to as qualified beats, and may be used to generate the template.

According to the method illustrated in FIG. 5, a template generation process involves combining a number of qualified cardiac beats to form a morphology template. Rate channel signals and shock channel signals of the qualified beats are sensed 502, 504. The peaks of the rate channel signals are identified 506 as fiducial points. The rate channel fiducial points are used to align 508 the corresponding shock channel signals of each qualified beat. The aligned shock channel signals are combined, for example, by averaging the aligned signals sample by sample. The value and location of features of the average shock channel waveform are determined relative to the rate channel fiducial points. In one implementation, the SVR template may be generated 510 using selected feature points extracted from the aligned shock channel waveforms. In another implementation, the template may be formed using all the samples of the shock channel waveforms. In yet another implementation, one or more morphological characteristics, such as QRS width, or other morphological characteristics, may be used to form the template.

Figure 6:
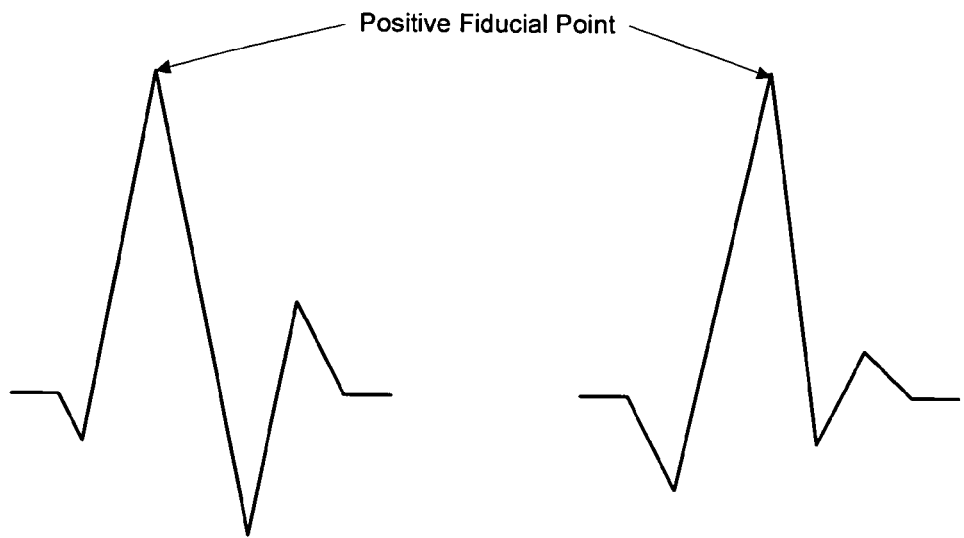
FIGS. 6 and 7 depict positive and negative fiducial points, respectively, the positive and negative fiducial points determined from rate channel signals in accordance with embodiments of the invention.
Figure 7:
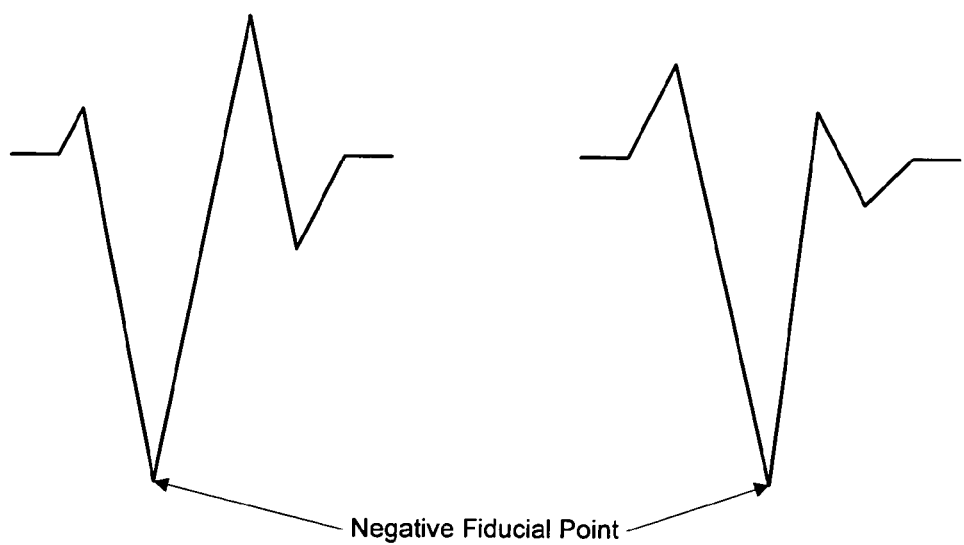

As previously discussed, a fiducial point represents a peak value of the rate channel signal. A fiducial point type may be either positive (Pos), associated with a positive peak, or negative (Neg), associated with a negative peak. When a template is formed, the positive peak (Pos) or the negative peak (Neg) of the rate channel signal used to form the template determines the fiducial point type of the template. FIGS. 6 and 7 depict positive and negative fiducial points, respectively. The Pos and Neg peaks are measured as absolute values. The fiducial point type is determined by Equation 1 as follows:

If Pos>0.9*Neg, the fiducial point type is positive

If Pos≤0.9*Neg, the fiducial point type is negative  [1]

If a stored template exists, the fiducial point type of the stored template is used as the fiducial point type of the template. If no stored template exists, the fiducial point type is determined using multiple qualified beats.

Figure 8:
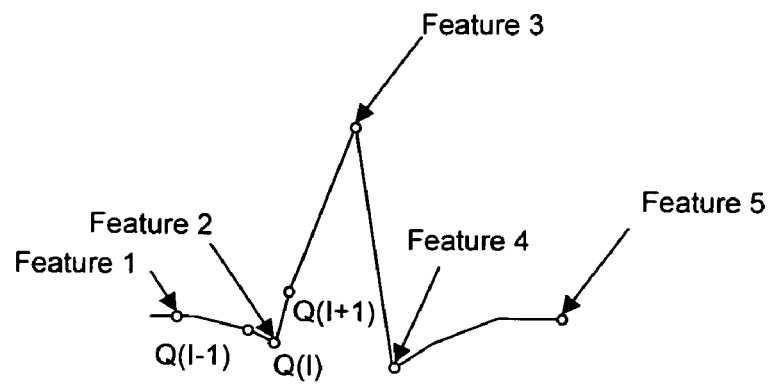
FIGS. 8 through 11 illustrate a process for selecting template feature points in accordance with embodiments of the invention.
Figure 9:
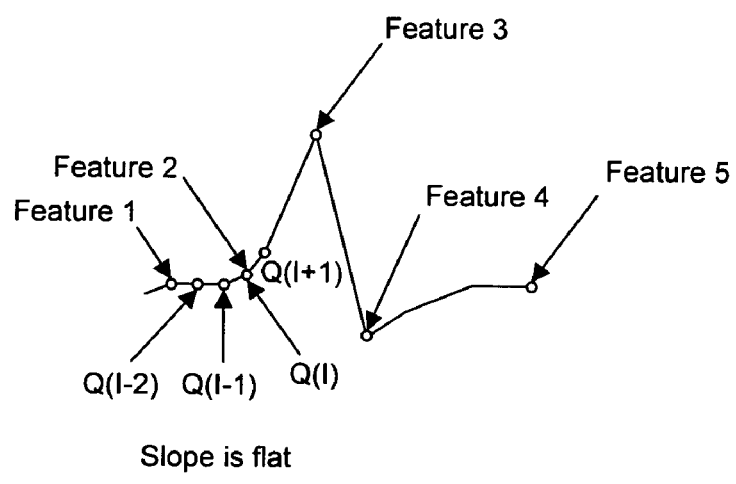

In one embodiment of the invention, and with reference to FIGS. 8 and 9, five features are initially identified for the SVR template, followed by three additional features determined at midpoints between certain ones of the five initially selected features.

Feature 3 is selected as the absolute maximum peak in a feature window defined by 31 samples centered at the fiducial point. If the positive peak amplitude is equal to the negative peak amplitude, the positive peak is selected as Feature 3.

Feature 2 is found by searching backward from Feature 3 until a point is reached that meets the following conditions: 1) the search is limited to 10 samples. If no point satisfies the following conditions, then the 10th sample becomes Feature 2; 2) the amplitude is less than 25% of the maximum peak; 3) a turning point is found or the slope is flat, and 4) Feature 2 is at least 4 samples away from Feature 3.

By way of example, let Q(I) represent the current sample. A turning point is found if:

$Q(I-1) \geq Q(I)$ and $Q(I) < Q(I+1)$ for a positive Feature 3

$Q(I-1) \leq Q(I)$ and $Q(I) > Q(I+1)$ for a negative Feature 3  [2]

As is shown in FIG. 8, Q(I) is selected as Feature 2. As such, Feature 2 is selected as a turning point.

The slope is considered flat, as shown in FIG. 9, if abs(Q(I+1)−Q(I−1))<4 and abs(Q(I+1)−Q(I−2))<4, in the case when the A/D converter maximum value is 128. In the illustrative depiction of FIG. 9, Q(I) is selected as Feature 2. As such, Feature 2 is selected as a flat slope point.

Feature 4 is found by searching forward starting from Feature 3 until a point is reached that meets the following conditions: 1) the search is limited to 16 samples. If no point satisfies the following conditions, then the 16th sample becomes Feature 4; 2) the amplitude is less than 25% of the maximum peak; and 3) a turning point is found or the slope is flat.

By way of example, let Q(I) represent the current sample. A turning point is found if:

$Q(I+1) \geq Q(I)$ and $Q(I) < Q(I-1)$ for a positive Feature 3

$Q(I+1) \leq Q(I)$ and $Q(I) > Q(I-1)$ for a negative Feature 3    [3]

Figure 10:
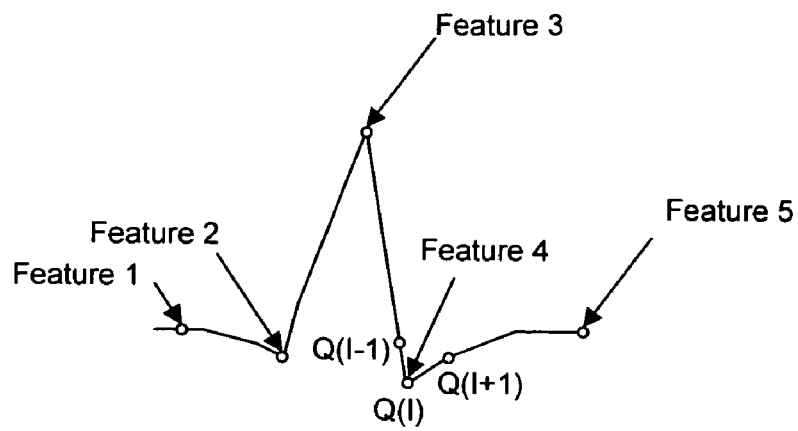

Q(I) is selected as Feature 4, as is shown in FIG. 10.

Figure 11:
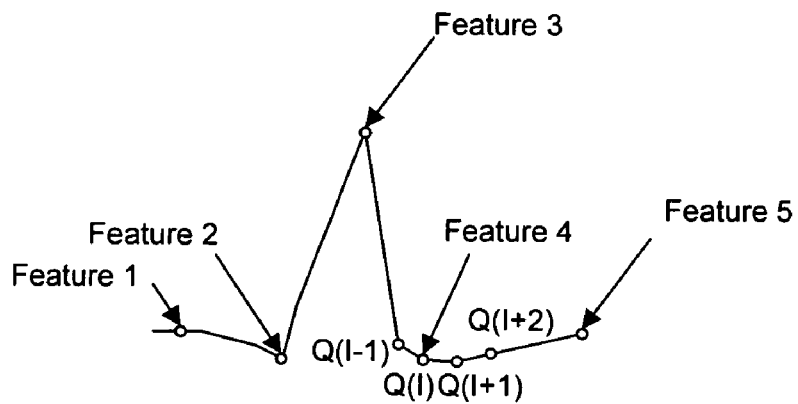

The slope is flat, as shown in FIG. 11, if abs(Q(I−1)−Q(I+1))<4 and abs(Q(I−1)−Q(I+2))<4. In this case, Q(I) is selected as Feature 4.

Feature 1 is selected as the seventeenth sample from the beginning of the detection window. Feature 5 is selected as the last sample of the detection window. Three additional features are selected at the midpoint of Features 1 and 2, the midpoint of Features 2 and 3, and the midpoint of Features 3 and 4, respectively. If a midpoint falls between two sample points, the leftmost (earlier in time) point is selected. Thus, according to this embodiment, eight feature values (e.g., amplitudes) and their associated locations with respect to the fiducial point and the corresponding fiducial point type are saved for SVR characterization.

Figure 12:
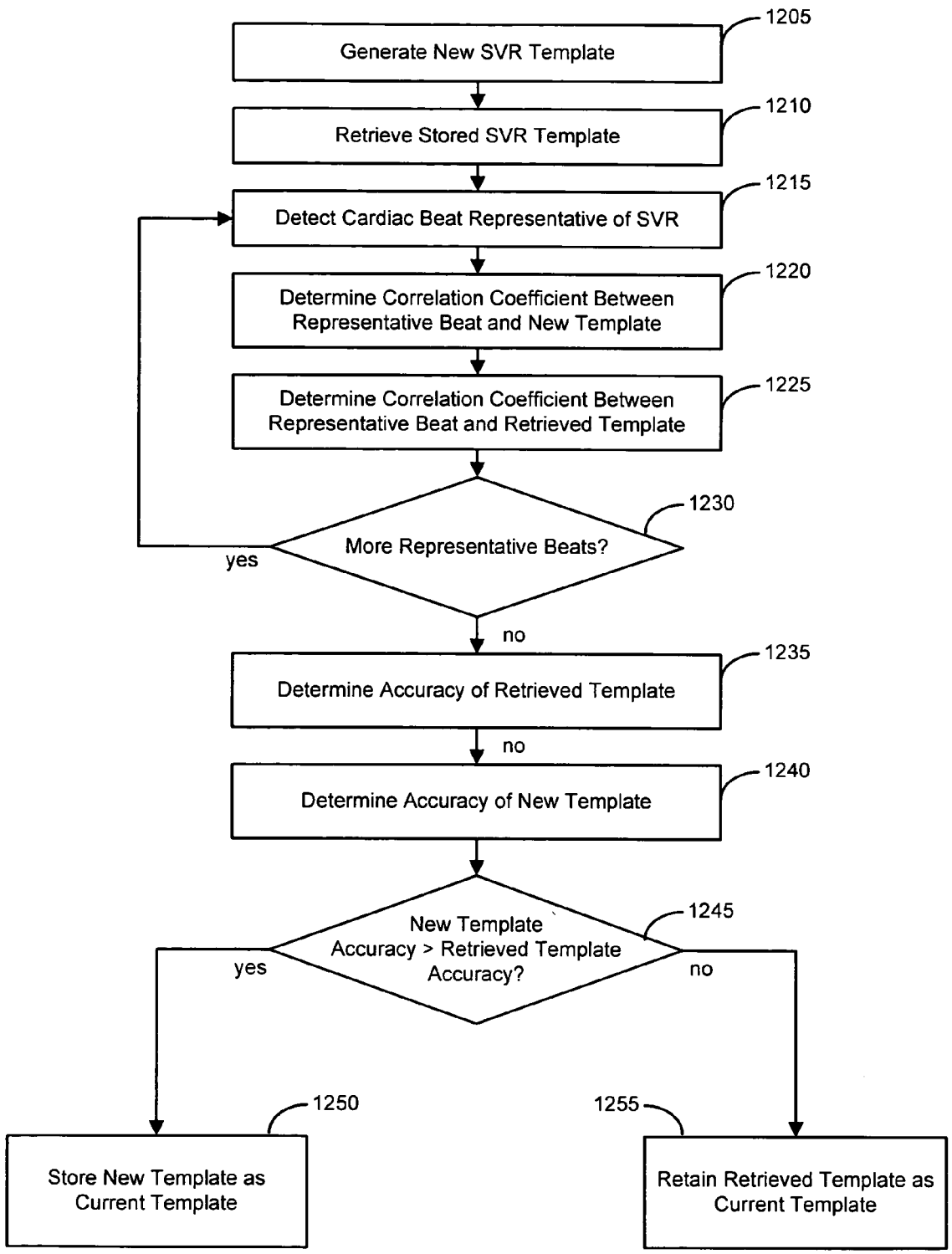
FIG. 12 is a flowchart illustrating a method of template selection based on a two channel SVR template generation process in accordance with embodiments of the invention.

FIG. 12 illustrates a method of template selection based on the two channel SVR template generation process described in connection with FIGS. 5–11. A new SVR template is generated 1205 in accordance with the two channel process. A current SVR template, which may be formed using the same process, is retrieved 1210 from memory. A set of cardiac beats representative of the patient's supraventricular rhythm is sensed and used to evaluate the current template and the new template. Evaluation of the current and new templates may involve, for example, calculating an average correlation between the set of representative beats and each of the templates, or by other methods.

The correlation between a template and a representative beat may be determined by calculating a feature correlation coefficient (FCC). In one particular embodiment, Equation 4, provided below, is used to compute the FCC between the template features and the beat features.

$$FCC = \frac{\left(N\sum_{i=1}^{N} X_i Y_i - \left(\sum_{i=1}^{N} X_i\right)\left(\sum_{i=1}^{N} Y_i\right)\right)^2}{\left(N\sum_{i=1}^{N} X_i^2 - \left(\sum_{i=1}^{N} X_i\right)^2\right)\left(N\sum_{i=1}^{N} Y_i^2 - \left(\sum_{i=1}^{N} Y_i\right)^2\right)} \quad [4]$$

where, Xi represents template N features and Yi represents beat N features, and N=8 in this illustrative example. The sign of the numerator term is checked before squaring. If the numerator is negative, the beat is uncorrelated, and the remainder of the computation need not be performed.

Alternatively, a generalized equation for computation of a correlation coefficient in accordance with a correlation waveform analysis (CWA) technique. An equation for calculation of the correlation coefficient (CC) using this technique may be determined according to Equation 5.

$$CC = \frac{N\sum_{i=1}^{N} X_i Y_i - \left(\sum_{i=1}^{N} X_i\right)\left(\sum_{i=1}^{N} Y_i\right)}{\sqrt{\left(N\sum_{i=1}^{N} X_i^2 - \left(\sum_{i=1}^{N} X_i\right)^2\right)\left(N\sum_{i=1}^{N} Y_i^2 - \left(\sum_{i=1}^{N} Y_i\right)^2\right)}} \quad [5]$$

where, Xi represents template N samples and Yi represents signal N samples in this illustrative example.

Turning back to FIG. 12, a representative beat is detected 1215 and the correlation between the representative beat and the new template is calculated 1220 according to the methods described above. The correlation between the representative beat and the current template is calculated 1225.

If more representative beats are used 1230 for template evaluation, the next representative beat is detected 1215 and the process described in blocks 1220–1225 is repeated until 1230 a sufficient number of representative beats, e.g., about 5 to about 25 beats, are detected 1215 to evaluate the templates.

The accuracy of the retrieved template and the new template are evaluated 1235, 1240 using the detected beats. If the new template accuracy is greater than 1245 the retrieved template accuracy, then the new template is stored 1250 as the current template. If the retrieved template accuracy is greater than or equal to 1245 the new template, then the retrieved template is retained 1255 as the current template.

A template selection process in accordance with embodiments of the invention may be employed in the selection of templates used in capture detection. As described above, one or more capture-related templates, e.g., captured response templates, pacing artifact templates, and/or evoked response templates, may be used in capture detection procedures such as beat-by-beat capture verification during pacing, or for capture detection during a threshold test.

Figure 13:
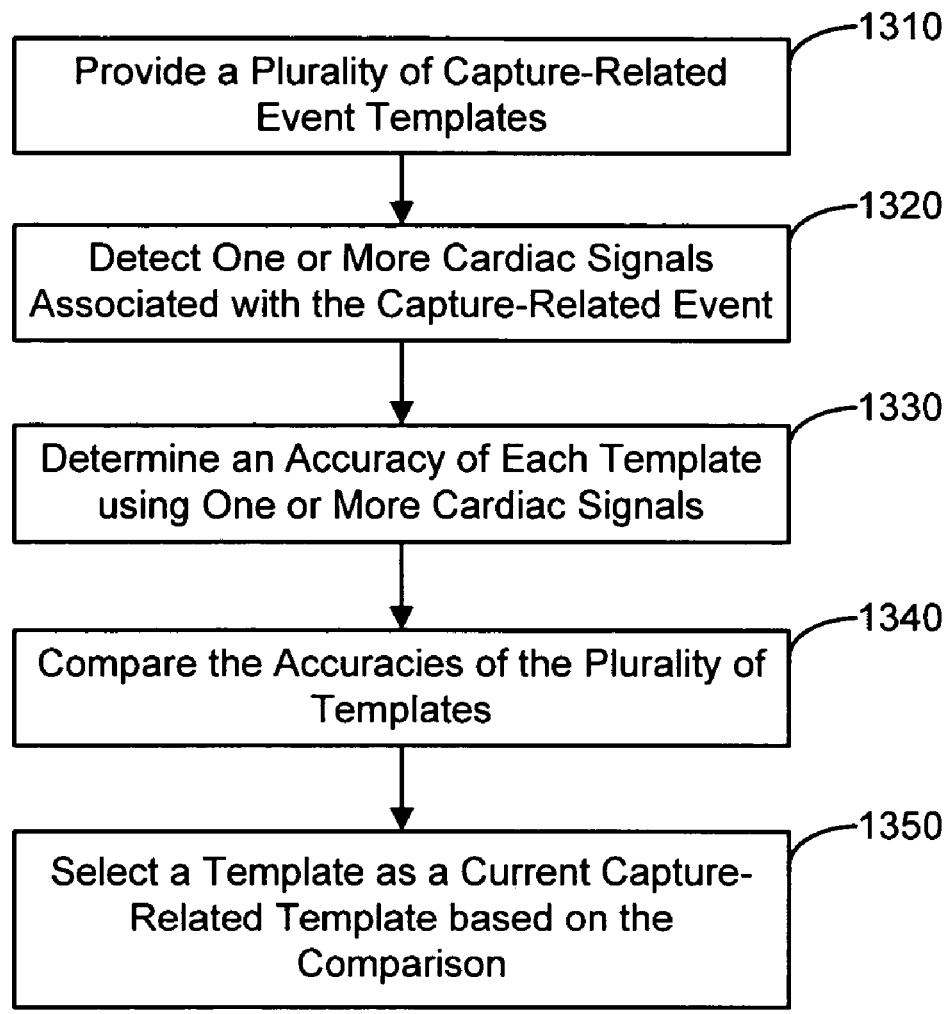
FIG. 13 is a flowchart illustrating a method of selecting capture-related templates in accordance with embodiments of the invention.

The flow chart of FIG. 13 illustrates a method of selecting capture-related templates in accordance with embodiments of the invention. A plurality of templates characterizing a particular type of capture-related event is provided 1310. For example, the templates may characterize an evoked response, a pacing artifact, a captured response, a fusion/pseudofusion beat, or any other event associated with capture.

The templates are evaluated using cardiac signals representative of the particular type of capture-related event characterized by the template. One or more cardiac signals representative of the type of capture-related event are detected 1320. The cardiac signals representative of the type of cardiac-related event may be used to determine 1330 the accuracy of the templates. In one embodiment, template accuracy is determined by evaluating the correlation between the cardiac signals representative of the type of capture-related event and a template characterizing the type of capture-related event. The accuracies of each of the templates are compared 1340. A template is selected 1350 as a current capture-related template based on the comparison. For example, a template having a highest average correlation with the cardiac signals representative of the capture-related event may be selected and stored as the current template.

In accordance with one approach, Equation 5 may be used for computation of the correlation coefficient. The number of samples associated with each capture-related waveform or template and used to determine the correlation coefficient is about 33 samples. Alternatively, fewer samples may be used to compute the correlation coefficient. For example, samples may be selected from the sensed capture-related signals and the capture-related template in accordance with a particular selection criteria, such as every fourth sample, for example. Correlation between the sensed capture-related signals and the template may be determined, for example, by calculating a feature correlation coefficient using the selected features of the template and cardiac signal in accordance with Equation 4 above.

The flowcharts of FIGS. 14A–14F illustrate methods of selecting a template in accordance with embodiments of the invention. Various methods of evaluating template accuracy are described.

Figure 14A:
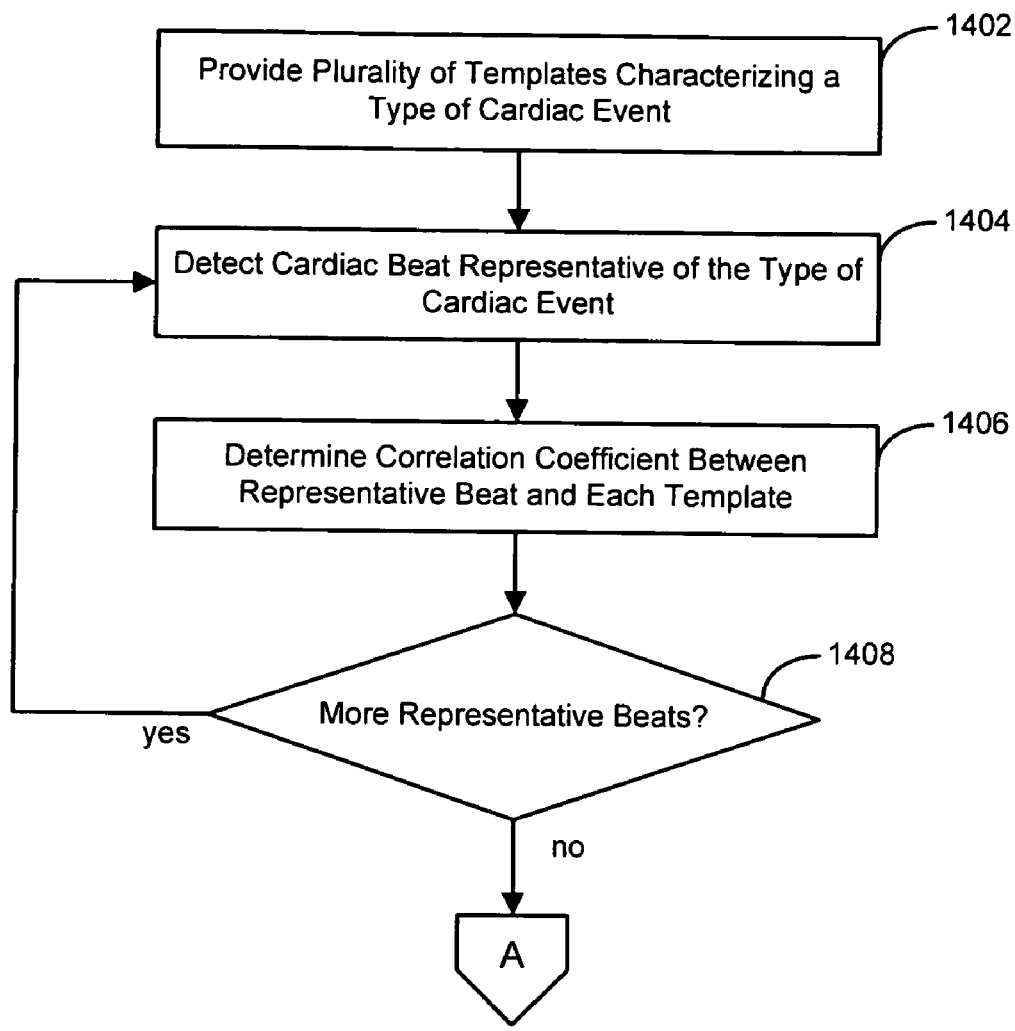

As illustrated in FIG. 14A, a plurality of templates characterizing a particular type of cardiac event are provided 1402. A set of cardiac beats representative of the type of cardiac event are detected 1404 for template evaluation. The correlation coefficient of a representative cardiac beat is calculated 1406 for each template. The process continues 1408 until a preset number of correlation coefficients have been calculated for each template.

Figure 14B:
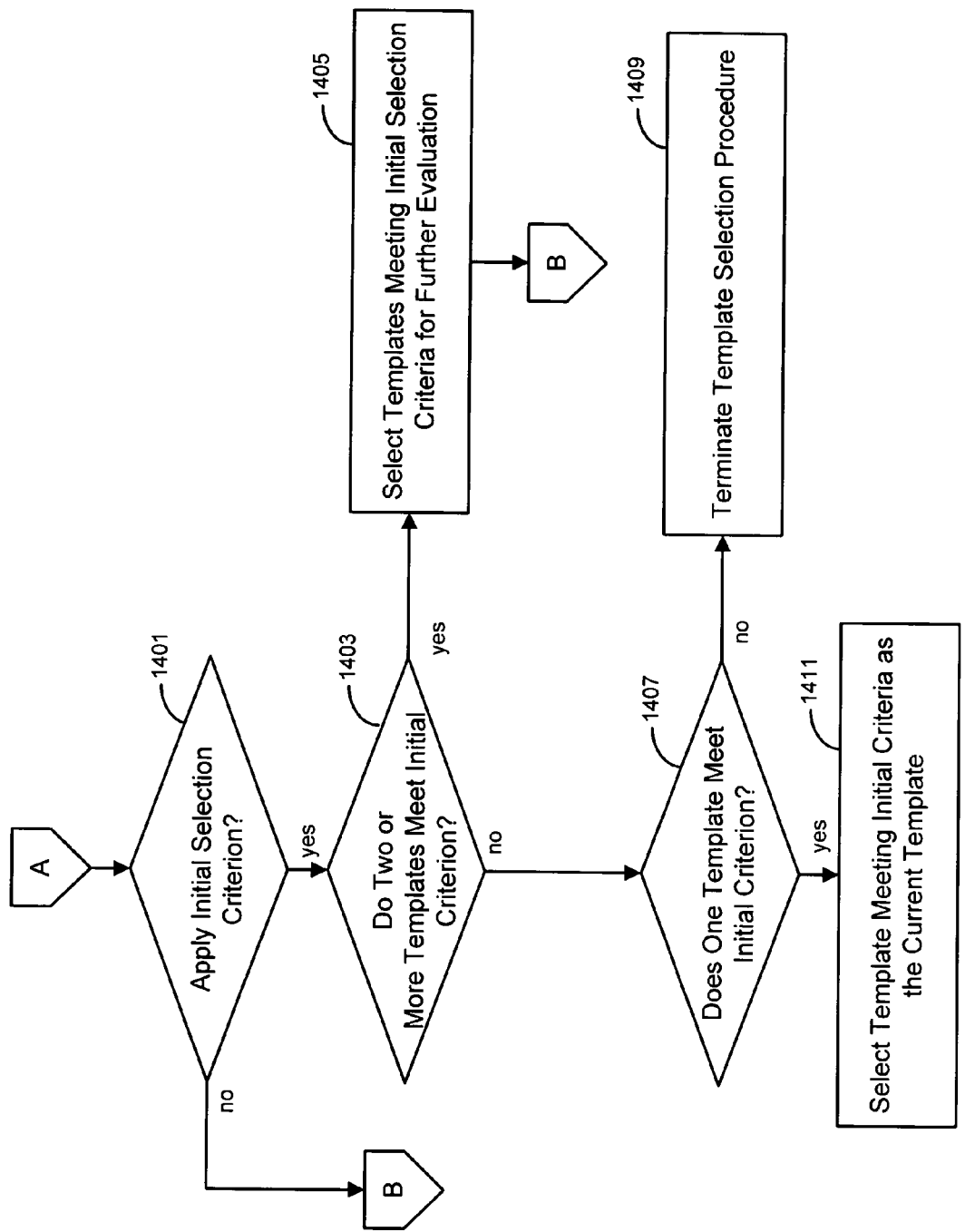

The flowchart of FIG. 14B follows from 14A and illustrates optional application of an initial template selection criterion. Final template selection may optionally be preceded by application 1401 of an initial selection criterion or criteria applied to each template, as illustrated in the flowchart of FIG. 14B. For example, the initial selection criterion may include a determination that the correlation coefficients calculated 1406 for each template meet or exceed a threshold value for at least N out of M representative beats. If two of more templates meet 1403 the initial criterion, then the two or more templates are further evaluated 1405 for template selection. If only one of the templates meets 1407 the initial criterion, then the template meeting the initial selection may be selected 1411 as the current template. Alternatively, the template selection process may be terminated if less than two templates meet the initial criterion. If no templates meet 1407 the initial criterion, then template selection is not possible and the procedure is terminated 1409. In this scenario, a currently stored template may be retained as the current template.

Figure 14C:
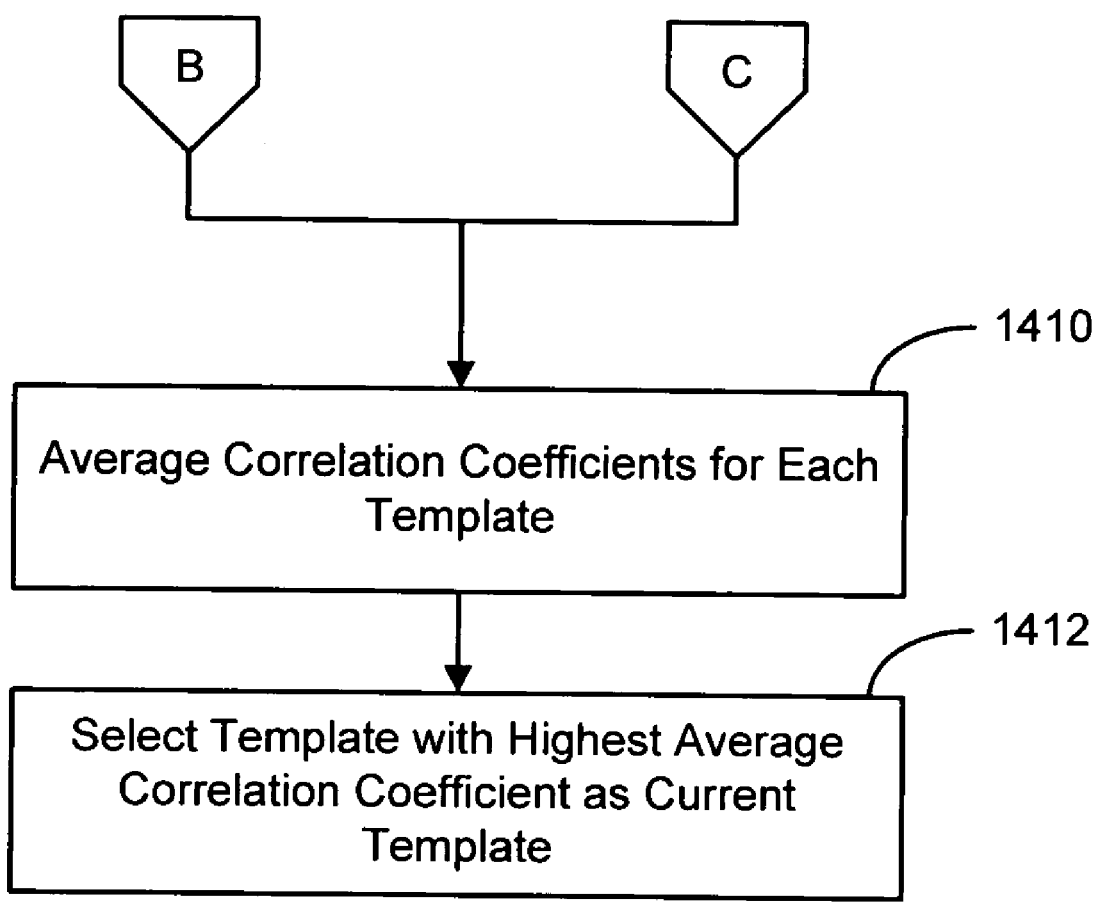
Figure 14D:
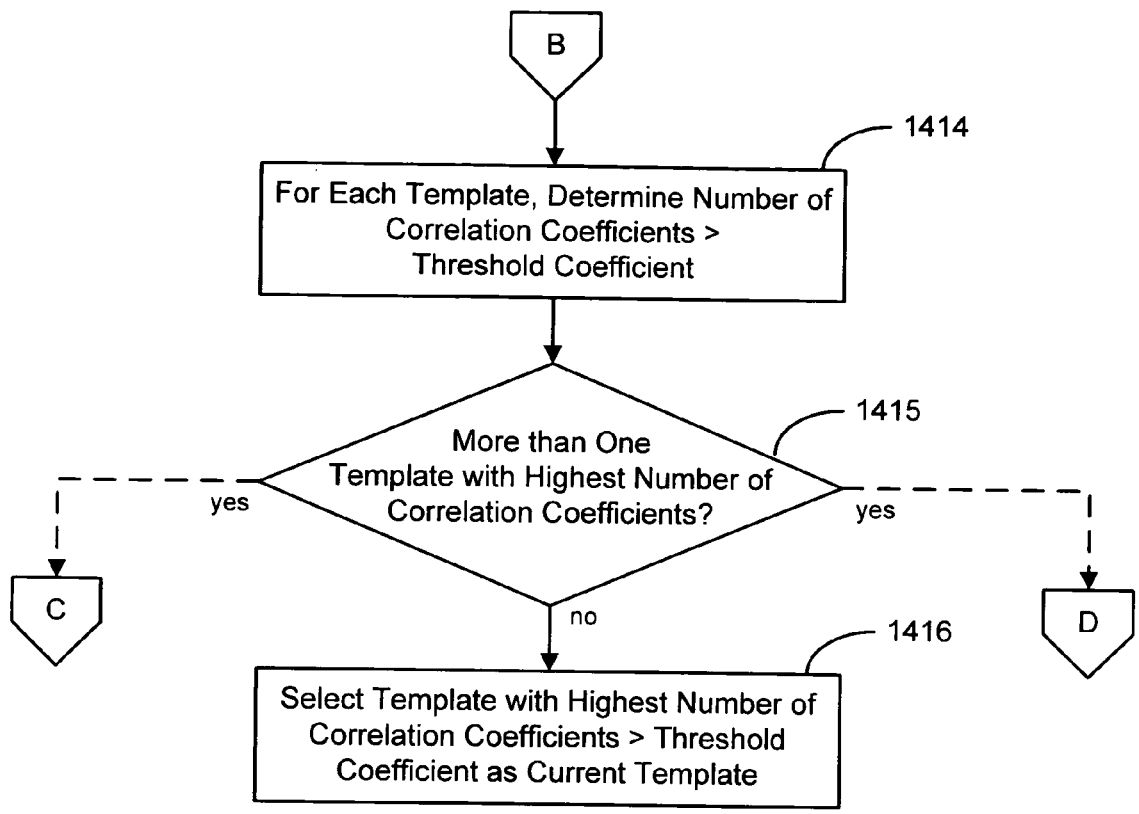
Figure 14E:
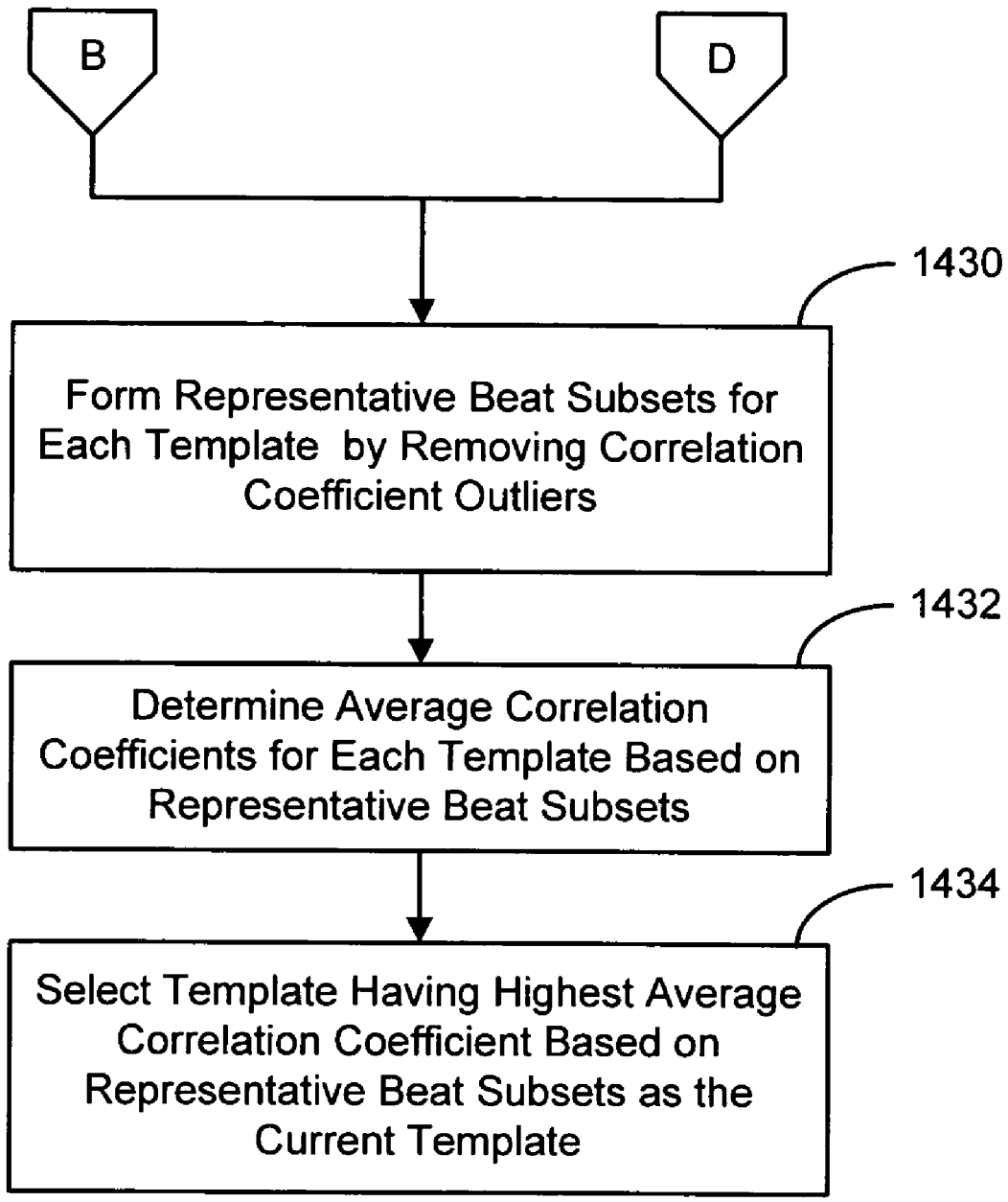

FIGS. 14C–14E illustrate various template selection methodologies that may follow from the optional process illustrated in FIG. 14B. In one embodiment, illustrated by FIG. 14C, the correlation coefficients determined for each template are averaged 1410. The template with the highest correlation coefficient average is selected 1412 as the current template.

In another embodiment, illustrated by FIG. 14D, the number of correlation coefficients greater than a threshold value is determined 1414 for each template. If there is a single template having 1415 the highest number of correlation coefficients greater than the threshold value, then that template is selected 1416 as the current template. However, if there are two or more templates that have the highest number of correlation coefficients greater than the threshold value, then final selection of the current template may be accomplished according to the processes illustrated in either FIG. 14C or FIG. 14E.

In the example illustrated by FIG. 14E, the selection criterion involves forming 1430 a subset of the correlation coefficients calculated for each template. For example, formation of the correlation coefficient subsets may involve removing one or more "outlier" coefficients from the set of correlation coefficients calculated for each template. Outlier coefficients may comprise the coefficients associated with the highest deviation from the average value of the set of correlation coefficients, for example. The subset of correlation coefficients are averaged 1432. The template having the subset of correlation coefficients with the highest average is selected 1434 as the current template.

Figure 14F:
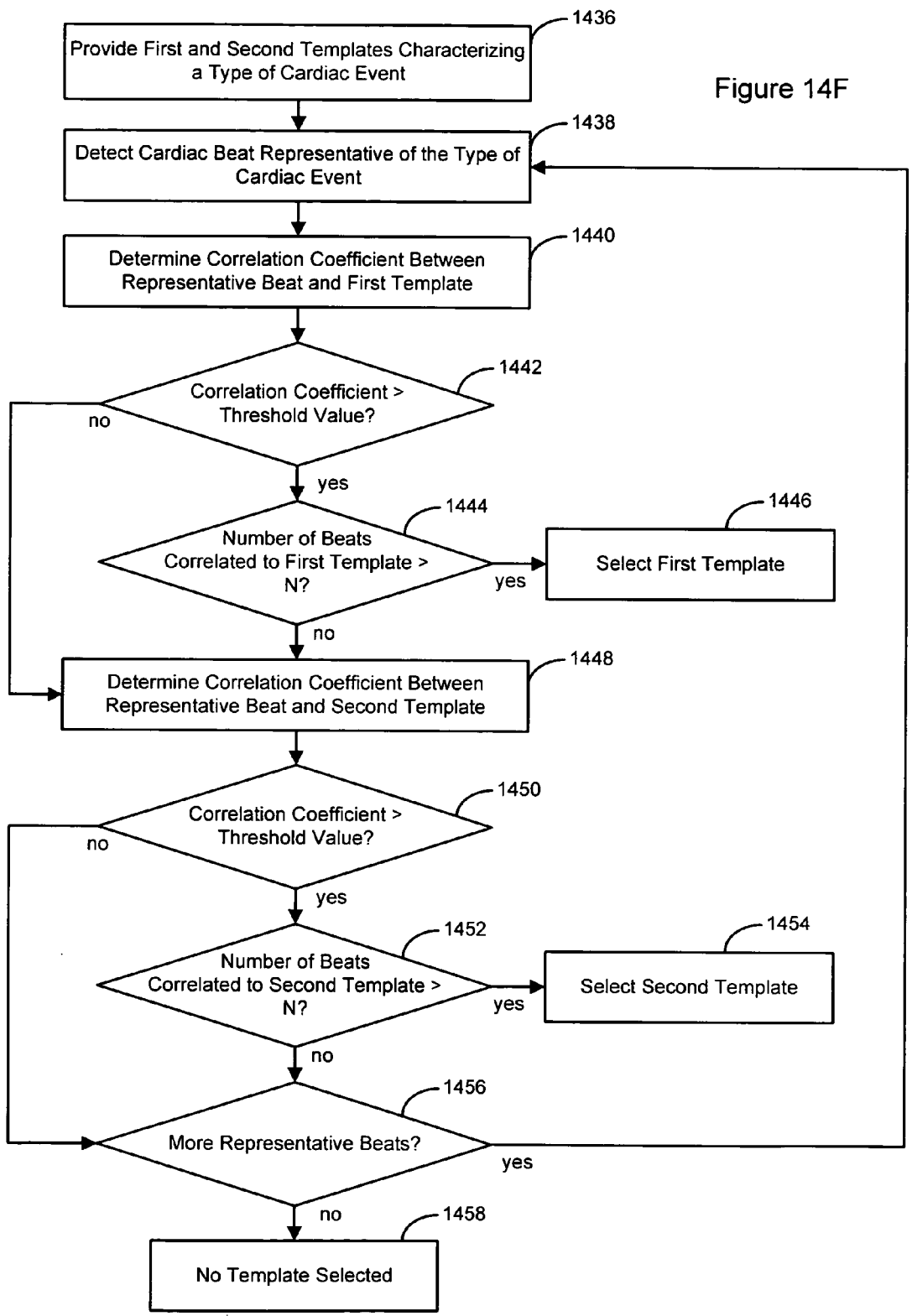

Yet another embodiment of template selection is illustrated by FIG. 14F. The implementation illustrated in FIG. 14F involves choosing the first template to achieve a selection criterion as the current template. In this example, first and second templates characterizing a cardiac event are provided 1436. A cardiac beat representative of the type of cardiac event is detected 1438. The correlation coefficient between the representative beat and the first template is determined 1440. If the correlation coefficient is greater than 1442 a threshold value, then the representative beat is considered to be correlated to the template. If the number of representative beats correlated to the first template is greater than 1444 a predetermined number, then the first template is selected 1446 as the current template.

If the representative beat is not correlated 1442 to the first template, or if the number of representative beats correlated to the first template is not greater than 1444 the predetermined number, then the second template is checked. The correlation coefficient between the representative beat and the second template is determined 1448. If the correlation coefficient is greater than 1450 a threshold value, then the representative beat is considered to be correlated to the second template. If the number of beats correlated to the second template is greater than 1452 a predetermined number, then the second template is selected 1454 as the current template.

If the correlation coefficient between the representative beat and the second template is not greater than 1450 a threshold value, or if the number of beats correlated to the second template is not greater than 1452 the predetermined number, then more representative beats may be acquired 1456. If neither template achieves the predetermined number of correlated beats, then no template is selected 1458, or a default template is used, e.g., a previously selected template.

The processes described herein may be used to select templates representing a number of types of cardiac events. The template selection methodologies described herein are not limited to arrhythmia-related template selection or to capture-related template selection. The embodiments described are provided as example implementations. A number of types of cardiac events may be characterized using templates. Accordingly, the templates characterizing these any of these event types may be selected using the processes described herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A morphology template selection method, comprising:
providing a plurality of templates representing a type of cardiac event;
evaluating one or more characteristics of each template, the one or more characteristics including template accuracy;
comparing the evaluations; and
selecting a template as a current template based on the comparison.

2. The method of claim 1, wherein providing the plurality of templates comprises retrieving at least one stored template from memory.

3. The method of claim 1, wherein providing the plurality of templates comprises generating at least one new template.

4. The method of claim 1, wherein the type of cardiac event comprises a sensed cardiac beat.

5. The method of claim 1, wherein the type of cardiac event comprises a paced cardiac beat.

6. The method of claim 1, wherein the type of cardiac event comprises a non-supraventricular conducted ventricular beat.

7. The method of claim 1, wherein the type of cardiac event comprises a supraventricular conducted ventricular beat.

8. The method of claim 1, wherein the type of cardiac event comprises a capture-related event.

9. The method of claim 1, wherein evaluating the one or more characteristics of each template comprises:
detecting cardiac signals associated with the type of cardiac event; and
evaluating each template using the cardiac signals.

10. The method of claim 1, wherein evaluating the one or more characteristics including the template accuracy of each template comprises determining a correlation between each template and one or more cardiac signals associated with the type of cardiac event.

11. The method of claim 1, wherein selecting the template as the current template comprises selecting a template having a higher accuracy.

12. A cardiac rhythm template selection method, comprising:
providing a plurality of templates representing a type of cardiac rhythm;
detecting one or more cardiac beats associated with the type of cardiac rhythm;
determining an accuracy of each template using the one or more cardiac beats;
comparing the accuracies of the plurality of templates; and
selecting a template as a current template representing the type of cardiac rhythm based on the comparison.

13. The method of claim 12, wherein providing the plurality of templates representing the type of cardiac rhythm comprises providing the plurality of templates representing a supraventricular rhythm.

14. The method of claim 12, wherein providing the plurality of templates comprises retrieving at least one template from memory and generating at least one new template.

15. The method of claim 12, wherein providing the plurality of templates comprises:
sensing cardiac signals using a first channel;
sensing cardiac signals using a second channel;
aligning the second channel signals using the first channel signals; and
forming a template using features selected from the aligned second channel signals.

16. The method of claim 15, wherein the first channel is a rate channel and the second channel is a shock channel.

17. The method of claim 12, wherein providing the plurality of templates representing the cardiac rhythm comprises providing at least one template comprising a set of feature points representing the type of cardiac rhythm.

18. The method of claim 12, wherein:
determining an accuracy of each template comprises determining correlation factors between the one or more cardiac beats and each template; and
comparing the accuracies comprises comparing the correlation factors.

19. A medical device, comprising:
a sensing system configured to sense electrical cardiac signals associated with cardiac events; and
a processor coupled to the sensing system and configured to provide a plurality of templates representing a type of cardiac event, evaluate one or more characteristics of each template, the one or more characteristics including template accuracy, compare the evaluations, and select a template as a current template representing the type of cardiac event based on the comparison.

20. The medical device of claim 19, further comprising a memory and wherein the plurality of templates includes at least one template retrieved from the memory and at least one new template.

21. The medical device of claim 19, wherein the plurality of templates comprises a plurality of templates representing a supraventricular rhythm.

22. The medical device of claim 19, wherein the plurality of templates comprises a plurality of templates representing a capture-related event.

23. The medical device of claim 19, wherein the processor is configured to evaluate the template accuracy of each template based on correlation coefficients associated with a similarity of each template and cardiac signals representative of the type of cardiac event.

24. The medical device of claim 19, wherein:
the electrical cardiac signals include rate channel signals and shock channel signals; and
the sensing system comprises a rate channel configured to sense the rate channel signals and a shock channel configured to sense the shock channel signals.

25. The medical device of claim 24, wherein the plurality of templates comprises at least one template representing a supraventricular rhythm formed based on the rate channel signals and the shock channel signals.

26. A medical system, comprising:
means for providing a plurality of templates representing a type of cardiac event;
means for evaluating one or more characteristics of each template, the one or more characteristics including template accuracy;
means for comparing the evaluations; and
means for selecting a template as a current template based on the comparison.

27. The system of claim 26, wherein means for providing the plurality of templates comprises means for storing at least one template and means for retrieving the at least one template from the storage means.

28. The system of claim 26, wherein means for providing the plurality of templates comprises means for generating at least one new template.

29. The system of claim 26, wherein the type of cardiac event comprises a sensed cardiac beat.

30. The system of claim 26, wherein the type of cardiac event comprises a paced cardiac beat.

31. The system of claim 26, wherein the type of cardiac event comprises a type of cardiac rhythm.

32. The system of claim 26, wherein the type of cardiac event comprises a capture-related event.

33. A medical system, comprising:
   means for providing a plurality of templates representing a type of cardiac rhythm;
   means for detecting one or more cardiac beats associated with the type of cardiac rhythm;
   means for determining an accuracy of each template using the one or more cardiac beats;
   means for comparing the accuracies of the plurality of templates; and
   means for selecting a template as a current template representing the type of cardiac rhythm based on the comparison.

* * * * *